United States Patent [19]

Downing, Jr.

[11] Patent Number: 5,796,481
[45] Date of Patent: Aug. 18, 1998

[54] SUSPENDED PARTICLE CONCENTRATION MONITOR

[76] Inventor: John P. Downing, Jr., 260 Kala Heights Dr., Port Townsend, Wash. 98368

[21] Appl. No.: 899,273

[22] Filed: Jul. 23, 1997

[51] Int. Cl.$^6$ ............................................. G01N 21/00
[52] U.S. Cl. ...................... 356/343; 356/342; 250/574; 250/575
[58] Field of Search .................... 356/335, 336–343, 356/432, 435, 442; 250/574, 575, 222.2

[56] References Cited

U.S. PATENT DOCUMENTS

| | | | |
|---|---|---|---|
| 3,586,862 | 6/1971 | Topol | 356/442 |
| 3,665,201 | 5/1972 | Shea et al. | 356/342 |
| 3,714,444 | 1/1973 | Carr et al. | 356/442 |
| 3,867,033 | 2/1975 | Hasinger | 356/342 |
| 4,099,875 | 7/1978 | McMahon et al. | 356/342 |
| 4,841,157 | 6/1989 | Downing et al. | 250/574 |
| 4,914,310 | 4/1990 | Jarofski | 250/574 |
| 5,280,272 | 1/1994 | Nagashima et al. | 340/630 |
| 5,506,679 | 4/1996 | Cooper et al. | 356/338 |

*Primary Examiner*—Hoa Q. Pham
*Attorney, Agent, or Firm*—Donald W. Marks

[57] ABSTRACT

A suspended particle concentration monitor includes near and far detector circuits with near and far elements sensing scattered visible or near infrared radiation projected into a fluid volume in which particle concentration is determined. The spacing and characteristics of the light sensitive elements and the gains of the near and far detector circuits are selected to produce generally equal peak signals at separate particle concentrations. A computer contains three tables each containing particle concentrations in respective portions of the particle concentration range being monitored. Based upon analysis of the near and far detector signals, one of the tables is selected and used to find the particle concentration corresponding to one of the near and far detector signals.

20 Claims, 9 Drawing Sheets

SUSPENDED PARTICLE CONCENTRATION MONITOR

TECHNICAL FIELD

The present invention relates to devices for monitoring suspended particle concentrations in fluids, and particularly to such devices employing radiation sources directing visible or near infrared radiation into a volume of the fluid with sensing elements detecting radiation scattered by the suspended particles.

BACKGROUND ART

As used herein, the term "light" refers to both visible radiation and near infrared radiation (i.e., radiation with a wavelength in the range from 400 nm to 2000 nm).

The prior art contains many devices which monitor particle concentration in a fluid by directing light radiation into a volume of the fluid and detecting a quantity of radiation scattered by the particles. It is well known that light radiation, in the visible and near-infrared spectra, scattered from particles having diameters in the range from 0.1 to 1000 microns suspended in a fluid can be measured with a suitable detector and used to estimate particle concentration, the mass of particles per unit volume of the fluid. This works in many clear fluids such as water, petroleum products, alcohol, brine, benzene, MEK, acetone, etc.

Generally such particle concentration monitors must be calibrated with the material which is being monitored. Different materials scatter light differently based upon particle size, composition, shape and other properties. Thus calibration of a monitor with one type of material will likely yield erroneous readings on a different type of material.

One deficiency of prior art light scatter based particle concentration monitors is that the detector response for a range of particle concentrations that can be monitored is limited. The quantity of scattered light impinging upon the light sensing element continuously increases from zero, when there are no particles, to a maximum or peak at some higher particle concentration, and thereafter decreases with increasing particle concentration until the suspended particles reach a concentration blocking and/or absorbing substantially all the light. Generally the estimated particle concentrations determined by the monitors are valid only in either the ascending or the descending range of light sensing response to increasing particle concentration.

SUMMARY OF INVENTION

It is an object of the present invention to construct a particle concentration monitor using scattered light having an increased range of measured valid particle concentrations.

The present invention is summarized in a suspended particle concentration monitor employing both near and far light sensing elements detecting scattered light (visible or infrared radiation) from particles in a fluid volume illuminated by a light source wherein the detected signal from the far sensing element exceeds the detected signal from the near sensing element in a first portion of a particle concentration range and wherein the detected signal from the near sensing element exceed; the detected signal from the far sensing element in a second portion of the particle concentration range. Determination of the appropriate portion of the particle concentration range based upon the near and far detected signals enables use of both the ascending and descending response to increasing particle concentration in determining particle concentration so that the detectable particle concentration range is substantially enlarged.

One feature of the invention is the recognition that the peak responses of respective near and far scattered light sensing elements occur at different particle concentrations and that appropriate selection of one or more parameters, such as (a) the relative spacing of the near and far light sensing elements from the light source, (b) the relative sizes and/or sensitivity of the near and far light sensing areas and/or (c) the relative gains of near and far detecting circuits, produces different particle concentration range portions in which the near and far detector signals exceed each other so that the corresponding range portions can be determined.

Additional features of the invention include the provision of a computer with at least first and second tables of particle concentrations corresponding to respective range portions determined by differences in the detected signals from the near and far scattered light sensing elements; and the adjustment of the peak magnitudes of detected near and far scattered light signals to be about equal (within a predetermined percent of each other) to bring about the far signal exceeding the near signal in one range portion and the near signal exceeding the far signal in another range portion.

Other objects, advantages and features of the invention will be apparent from the following description of the preferred embodiments and/or the accompanying drawings.

DESCRIPTION OF THE PREFERRED EMBODIMENTS

Figure 1:
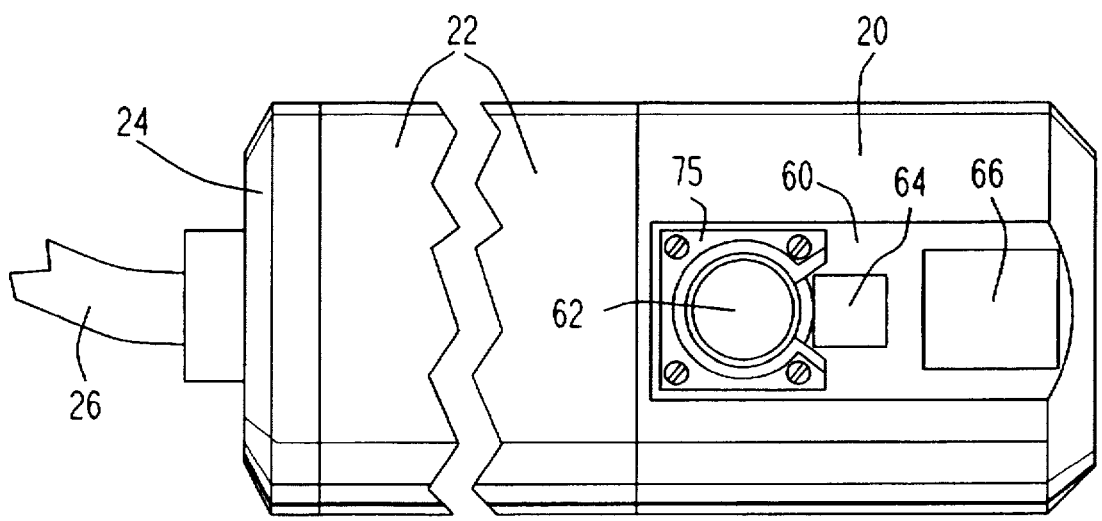
FIG. 1 is a plan view, with a center section broken away, of a suspended particle concentration monitor in accordance with the invention.
Figure 2:
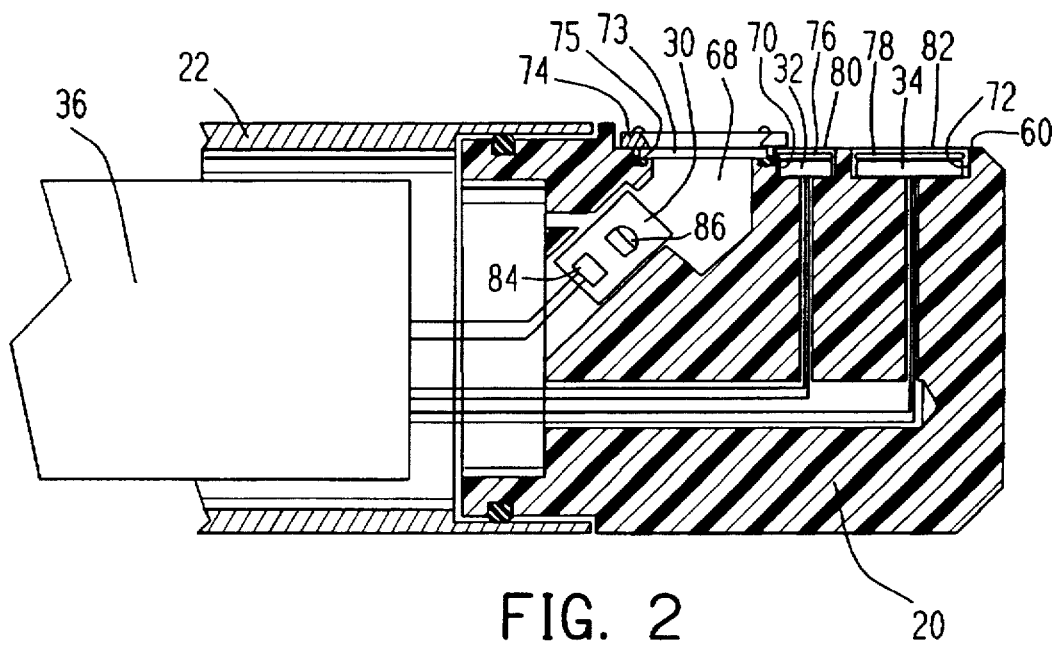
FIG. 2 is a section view of a head end portion of the monitor of FIG. 1.
Figure 5:
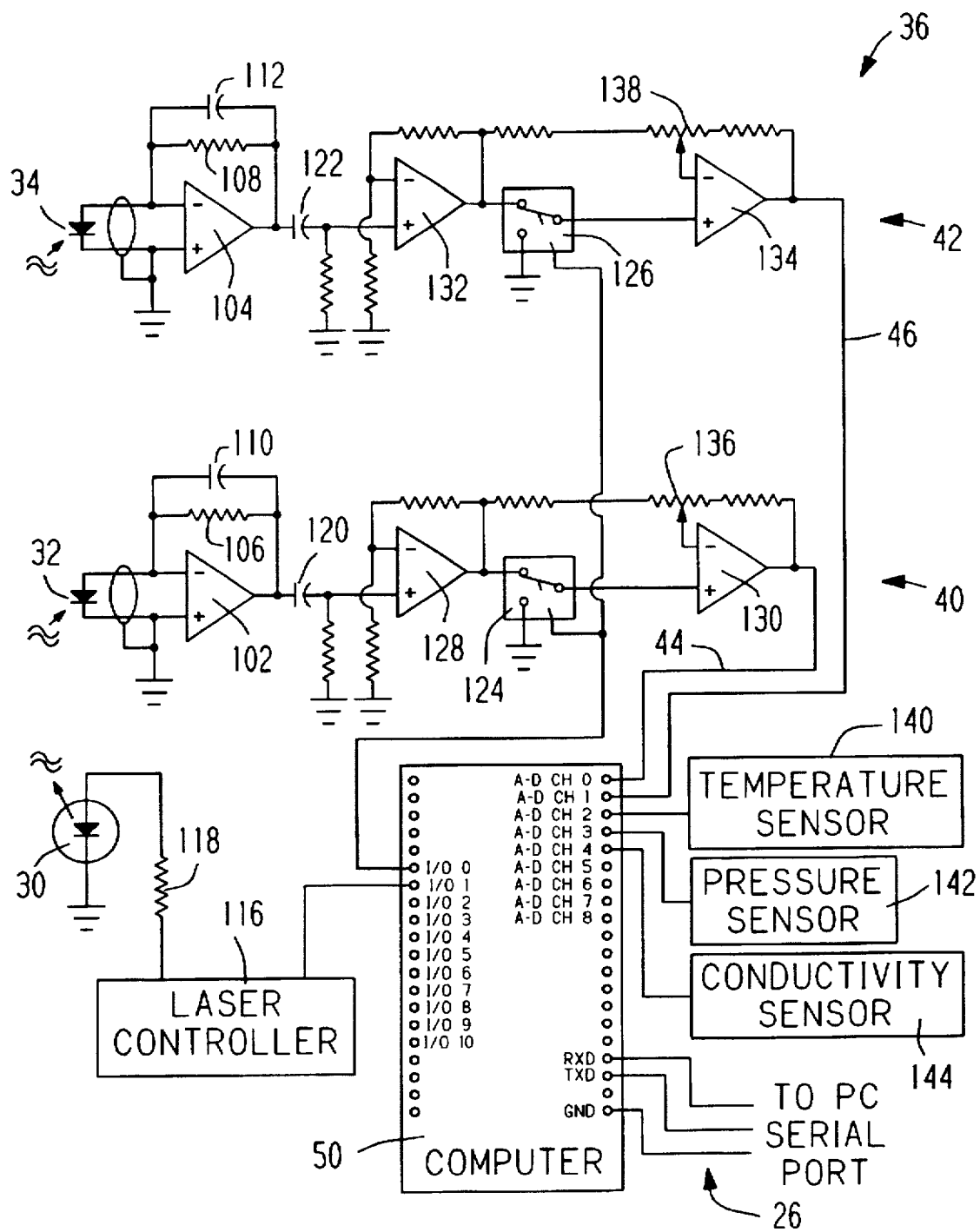
FIG. 5 is a schematic diagram of functional portions of electrical circuitry in the monitor of FIGS. 1 and 2.
Figure 6:
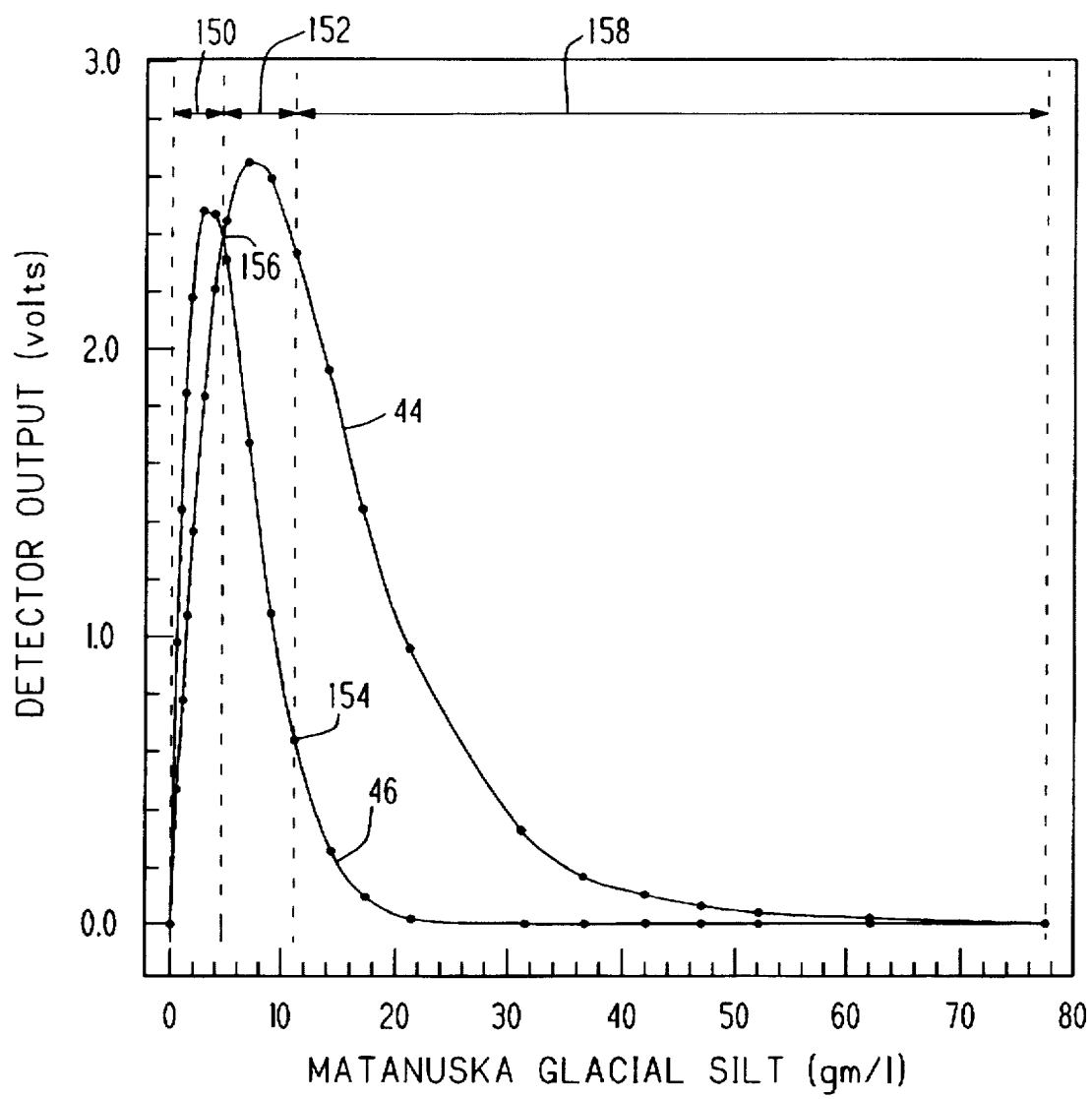
FIG. 6 is a graph illustrating an example of output responses relative to particle concentration at one selected calibration of near and far detector circuits in the circuitry of FIG. 5.
Figure 9:
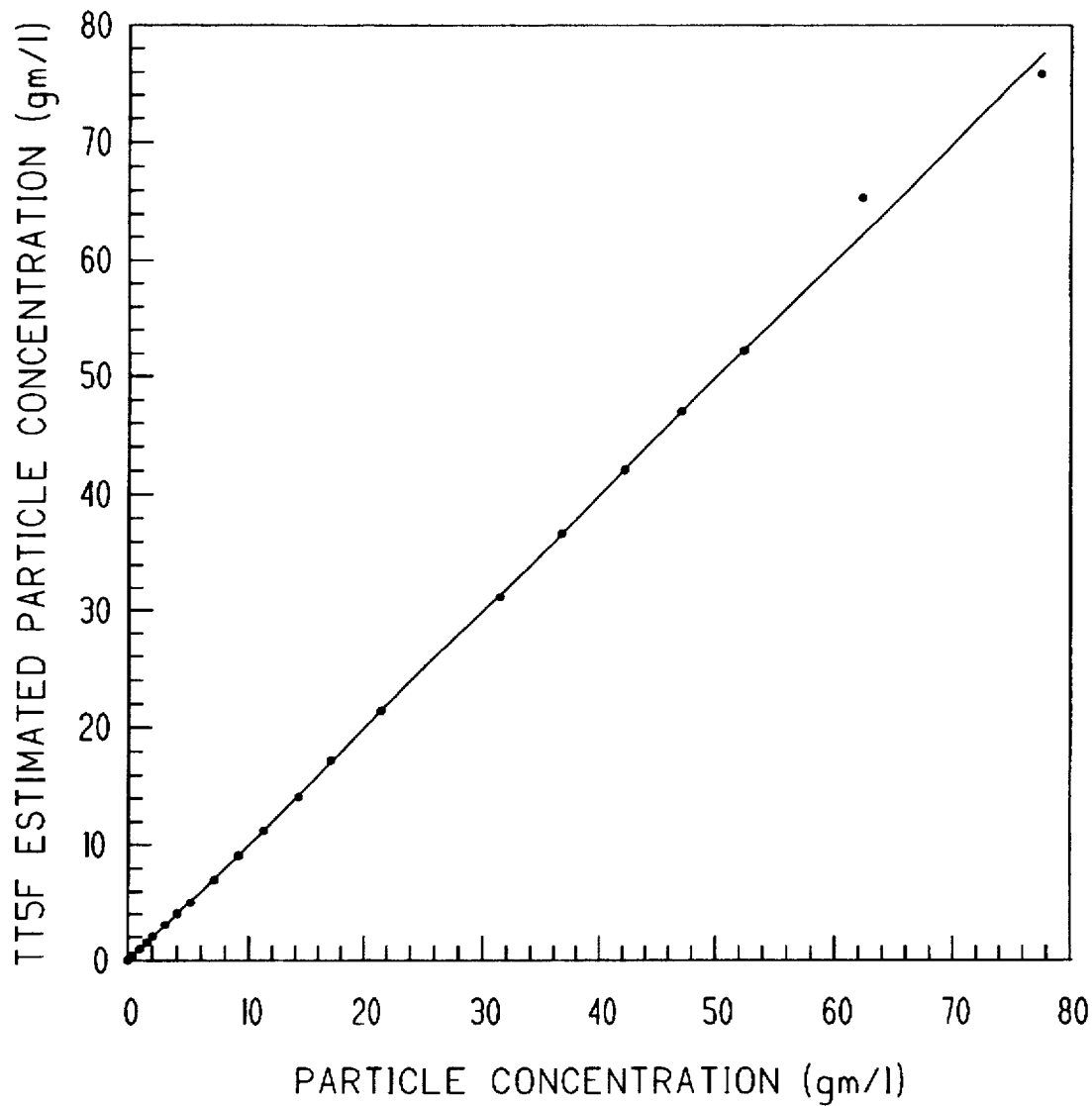
FIG. 9 is a graph illustrating accuracy of the data of detected particle concentrations by the procedure of FIG. 8 compared to actual particle concentrations.

As shown in FIGS. 1 and 2, a suspended particle concentration monitor in accordance with one embodiment of the invention is contained in a housing formed by a head 20 mounted on one end of a tubular center section 22 which has its opposite end closed by a cap 24. A cable 26 extending through the cap 24 connects the monitor to a remote processing or recording unit. Mounted within the head 20 are a light source 30, a near light sensitive element 32 and a far light sensitive element 34 which are all connected by wires to electric circuitry 36 supported within the center section 22. The electric circuitry 36, as illustrated in FIG. 5, includes a near detector circuit 40 for the near light sensitive element 32 and a far detector circuit 42 for the far light sensitive element 34. The characteristics of the respective sensing elements 32 and 34 and/or the gains of the detector circuits 40 and 42 are selected to produce respective near and far detector output signals as illustrated by respective curves 44 and 46 in FIG. 6 having, for one portion of the detectable particle concentration range, the far detector signal 46 exceeding the near detector signal 44 and, for another portion of the detectable particle concentration range, the near detector signal 44 exceeding the far detector signal 46. Referring back to FIG. 5, the near and far detector outputs 44 and 46 are received by corresponding inputs of an analyzing circuit such as a computer 50 which analyzes the far and near detector signals to determine a particle concentration. As shown in FIG. 9, the determined particle concentration (TT5F estimated particle concentration) for the example responses of FIG. 6 is accurate for an extended range of particle concentrations including both the ascending and the descending portions of the response curves of FIG. 6.

The head 20, as shown in FIGS. 1 and 2, is formed from a molded polymer, such as a black 20% glass filled polycarbonate or NORYL®, with a generally cylindrical shape. A flat surface 60 is formed in the cylindrical wall with windows 62, 64 and 66 opening into corresponding recesses 68, 70 and 72 in which the respective light source 30, near light sensitive element 32 and far light sensitive element 34 are contained. The window 62 for recess 68 for the light source 30 is closed by a window such as a sapphire window 73 transparent to the radiation of the light source. A metal retainer 74 secures the window to the head 20 and an O-ring 75 seals the window 73 over the recess. Filters such as Wratten filters 76 and 78 cover the respective light sensitive elements 32 and 34 to block light frequencies differing from a desired frequency. Clear epoxy 80 and 82 closes the windows 64 and 66.

Any near infrared or visible light source can be used for the light source 30 so long as it can be rapidly switched on and off or mechanically chopped. In a preferred embodiment, a laser diode 84 generating near infrared light is used because it is compact, easily switched electronically, and the radiation from it is rapidly attenuated by water. For example, at a wavelength of 780 nm, light transmission is attenuated by about 10% after travelling five centimeters in clean sea water whereas blue light (400 nm) is attenuated by only about 0.1% over the same distance. In a preferred scattered light monitor wherein the measurement volume is restricted (for example, to about five cubic centimeters over the windows) employment of infrared radiation is preferred. An example of a suitable near infrared light source is a SHARP laser diode model LT023WSO. Additionally the light source 30 can include a collimator such as an OPTIMA lens collimator 86 model LDM 3956KIT to intensity the light in the illuminated volume of fluid in which particle concentration is being measured.

A variety of light sensitive elements, such as photomultiplying, photoconductive, and photovoltaic devices, avalanche photodiodes, etc., can be used for the near and far light sensitive elements 32 and 34 so long as the elements are sensitive to light radiation from the source and can respond to rapidly chopped light. Square large-area photodiodes, such as HAMMATSU photodiodes models S1227-66BR and S1227-1010BR, are suitable for the elements 32, because their peak quantum efficiency occurs at nearly the same wavelength (780 nm) of light emitted by the selected laser diode 84.

Figure 3:
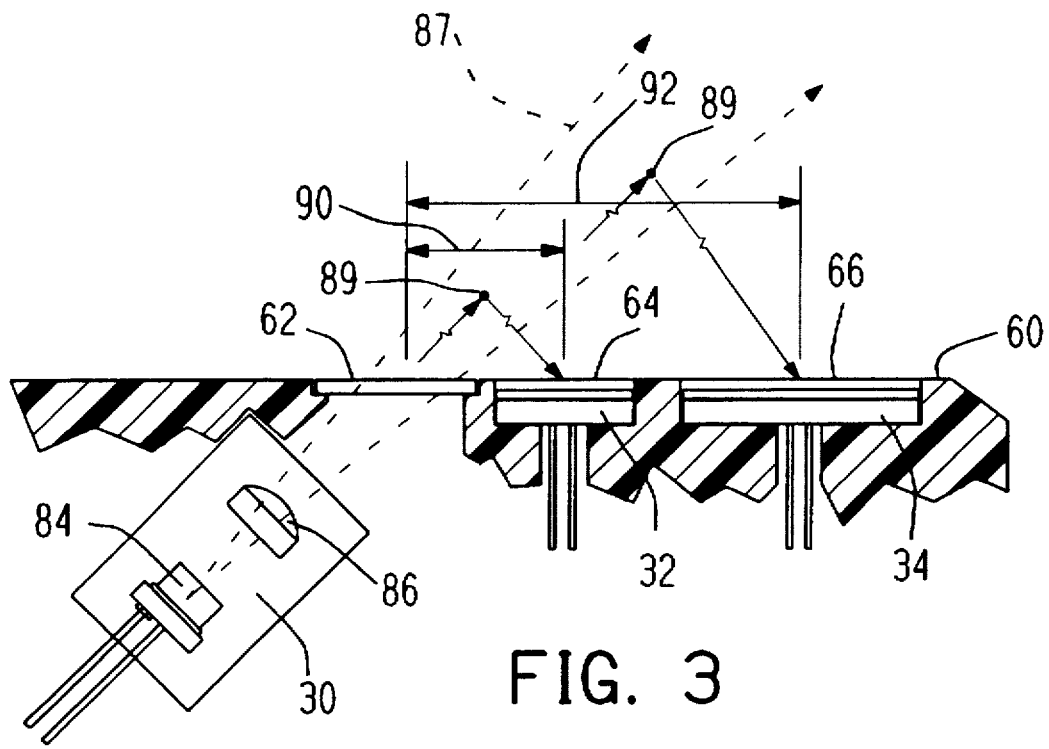
FIG. 3 is a diagrammatic sectional illustration of an arrangement of a light source with near and far light sensitive elements in the monitor of FIGS. 1 and 2.
Figure 4:
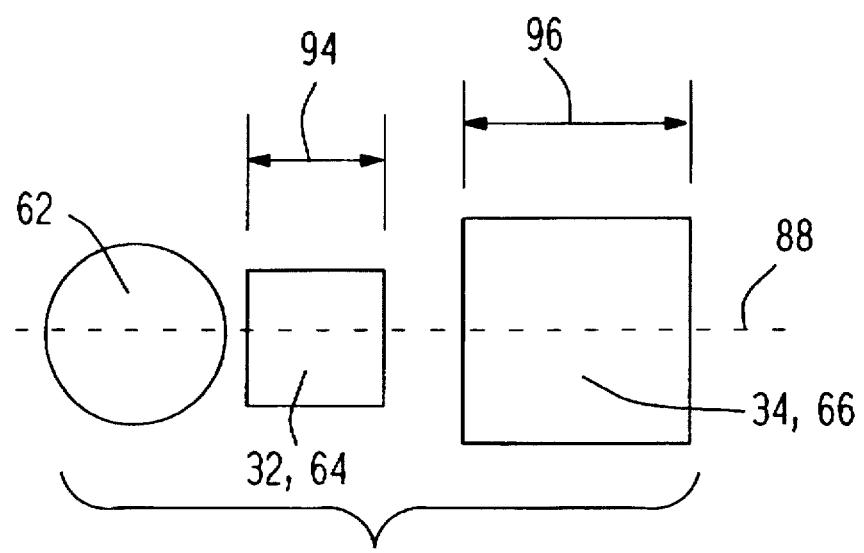
FIG. 4 is a diagrammatic plan illustration of the arrangement of the light source with near and far light sensitive elements of FIG. 3.

There are many combinations of optical geometries that can be used to produce the near and far detector responses from a single light source. These combinations include monitors employing forward scattered light, side scattered light, back scattered light, or a combination of two or all of the forward, side and back scattered light. The arrangement of the light source 30 and the near and far light sensitive elements 32 and 34 in FIGS. 1 and 2 employs mainly forward and side scattered light but back scattered light also contributes to the near and far detector signals particularly at low particle concentrations where the emitted light penetrates the fluid to greater distances from the light source. Generally as shown in FIGS. 3 and 4, the windows 62, 64 and 66 exposing the light source 30, the near light sensitive element 32 and the far light sensitive element 34, respectively, are in a common plane with the flat surface 60 of the head 60, and are aligned along a line 88 extending in the common plane 60. The light source 30 is oriented so that it projects a collimated beam 87 of light at an angle of about 45° over the windows 64 and 66 in a normal plane intersecting the flat surface at the line 88. The light sensitive elements 32 and 34 are parallel to each other and the common plane 60 to efficiently respond to light scattered by particles 89 and impinging on the windows 64 and 66.

Referring to FIG. 3 the center of the near light sensitive element 32 is positioned at a distance 90 from the center of the light beam 87 exiting the window 62 and the center of the far light sensitive element 34 is positioned at a distance 92 from the center of the light beam exiting the window 62. The near light sensitive element 32 is positioned as close as practical from the light source so that the distance 90 is limited by the sizes or geometry of the near light sensitive element and the light source, and the geometry of additional optic elements such as lenses, fiber optics, etc. For commercially available components, the distance 90 of the near sensitive element from the light source can vary from about 2 to about 10 millimeters.

The separation between the peaks of the near and far detector responses 44 and 46, FIG. 6, increases with increasing ratio of the distance 92 to the distance 90, i.e., the ratio of the distance of the far sensor 34 from the light source to the distance of the near sensor 32 from the light source. For increasing ratios over about 2, the rate of increase of peak separation decreases. Additionally, positioning the far light sensing element farther from the light source decreases the signal produced by the far light sensing element. Thus a ratio of distances of the far light sensing element to the near light sensing element in the range from about 2 to 4 is preferred for the employed components. This ratio corresponds to a distance 92 in the range from about 4 to 40 millimeters. Larger or more sensitive light sensors could be employed to produce corresponding changes in the preferred spacing of the sensors from the light sources.

Additionally, a larger sensing area for the far light sensitive element 34 is employed to compensate for the decline in signal strength resulting from light absorption and scattering and from beam spreading along the mean length of the path from the light source to the far light sensitive element 34. As shown in FIG. 4. the square near light sensitive element 32 has a width 94 while the square far light sensitive element 34 has a width 96 which is substantially larger than the width 94. For example, the width of the near light sensitive element 32 can be 9 mm while the width of the far light sensitive element 34 can be 15 mm resulting in the far light sensitive element 34 having about 2.8 times the light gathering area of the near light sensitive element 32 to render the far light sensitive element more sensitive.

In the circuit of FIG. 5, the signals generated by the light sensing elements 32 and 34 are applied to inputs of respective operational amplifiers 102 and 104 having respective feedback gain control resistances 106 and 108 along with high frequency noise filtering capacitors 110 and 112. The values of the gain control resistances 106 and 108 are selected to control the gains of the respective near and far detector circuits 40 and 42 to produce a detected peak far signal which is about equal to a detected peak near signal such as in FIG. 6. Generally the magnitudes of the far and near detector signal peaks should be within about 30% of each other and preferably within about 10% of each other to be considered about equal to each other. Generally the gain of the far detector circuit 42 is greater than the near detector circuit 40 to produce the equal peaks in the near and far detector signals.

The computer 50, in response to a conventional timer interrupt or other timed procedure, generates a square wave control signal which is applied to a laser controller 116 to turn the laser diode of the light source 30 on and off at a selected frequency such as a frequency in the range from 200 to 20,000 Hertz. When on, the laser diode is controlled by the controller 116 to produce constant illumination power. The amplified signals from the amplifiers 102 and 104 are applied by respective coupling capacitors 120 and 122 to respective synchronized detector circuits having respective electronic switches 124 and 126 operated by the computer 50 in synchronism with the light source 30. The switches 124 and 126 alternately connect ground and the outputs of unity gain amplifiers 128 and 132 to the positive input of unity gain amplifiers 130 and 134 making the amplifiers 130 and 134 as voltage inverters and voltage followers (i.e., alternating between gains of plus one and minus one) to produce DC outputs indicative of the magnitude of the AC signal from the light sensitive elements. Variable resistances 136 and 138 are adjusted to balance the synchronized detector circuits to eliminate any AC component.

The computer 50 is a conventional data processing unit having a CPU, ROM, RAM, non-volatile memory, and analog to digital converters, such as computer model TT5F. The outputs of the near and far light detector circuits 40 and 42 are applied to analog inputs of the computer 50 along with any other analog signals from other sensing devices such as a temperature sensor 140, a pressure sensor 142 and a conductivity sensor 144. The non-volatile memory contains look-up tables which are used by the computer 50 to convert either the reading of the near detector signal or the reading of the far detector signal into a corresponding particle concentration value. These tables are calculated and stored in the non-volatile memory during calibration of the particle concentration monitor.

Calibration of the monitor is performed by starting with a known volume of clean water in a vessel, a stirring mechanism for the water in the vessel, and a sufficient quantity of dried, disaggregated particles for which sensing calibration is being made. The monitor unit is positioned in the vessel to be sufficiently spaced so as not to be affected by the vessel walls, the stirring device or the surface of the water. Readings are then taken of the near and far detector signals produced in the clear water. A measured quantity of the particles is added and stirred in the vessel and readings are again taken and recorded of the near and far detector signals. The addition of a measured quantity of particles and the taking and recording of readings of the near and far detector signals is repeated for the range of particle concentrations to be monitored. Once the readings have been completed, such as shown by the dots in FIG. 6, the curves 44 and 46 can be generated by a computer mathematical process such as a "spline" fit. From these curves, the range of particle concentrations to be monitored can be divided in two or more portions. For an extended range of particle concentrations to be monitored, three portions is generally sufficient. For example in FIG. 6, a first range portion 150 of particle concentrations is defined by the region where the far detector signal 46 exceeds or is equal to the near detector signal 44. A second range portion 152 is defined by the region where the near detector signal 44 exceeds the far detector signal and the far detector signal 46 is greater than a minimum value such as at point 154 but less than a maximum value such as at point 156. A third range portion 158 is defined by the region where the far detector signal 46 is less than the minimum value 154 and the near detector signal 44 exceeds the far detector signal 46.

Figure 7:
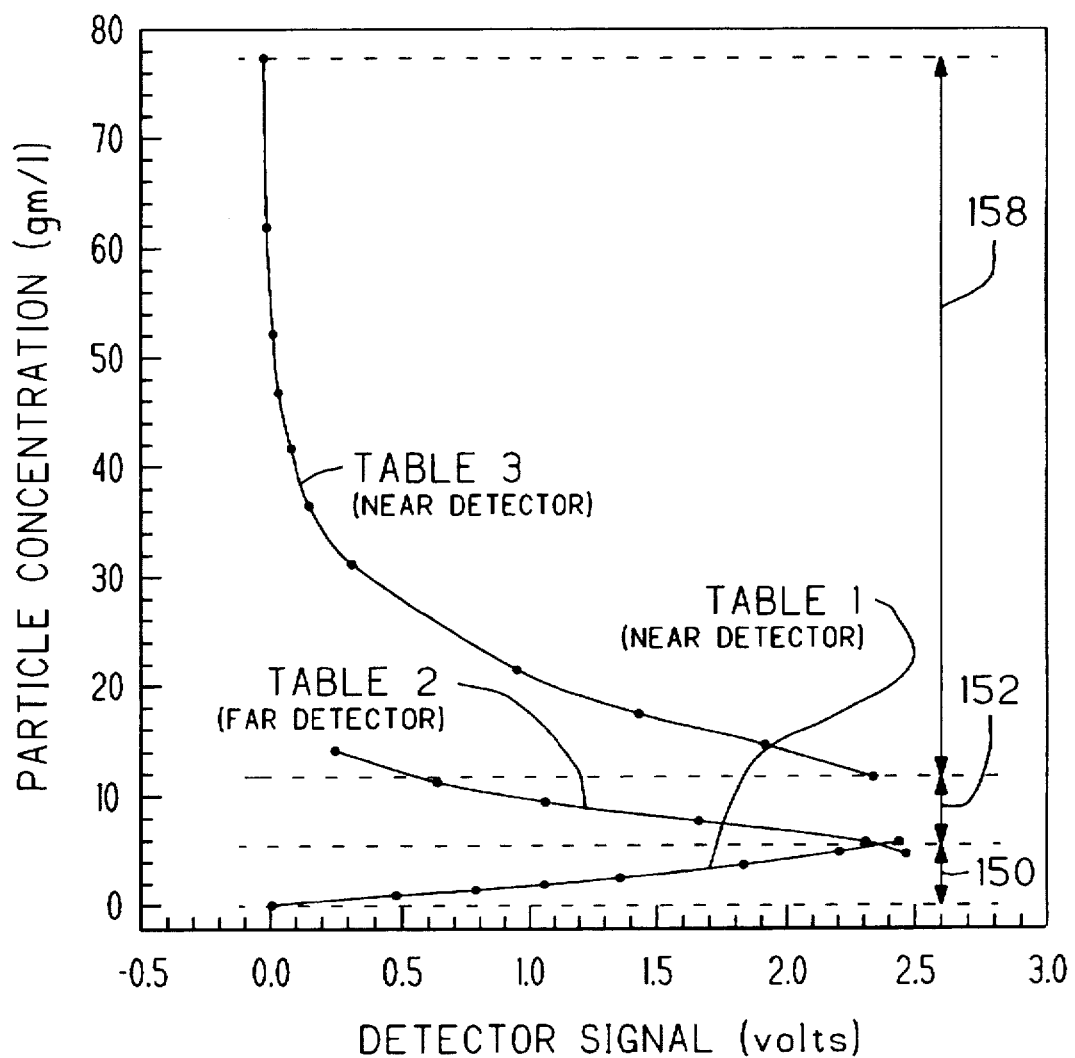
FIG. 7 is a graph illustrating contents of three tables calculated from the response curves of FIG. 6.

After the range portions have been defined, corresponding tables such as first, second and third tables (tables 1, 2 and 3 in FIG. 7) are generated and stored in the non-volatile memory of the computer 50 along with the minimum and maximum point values 154 and 156. For example, the first table contains corresponding particle concentrations for each voltage increment, such as 12-bit accuracy, of the near detector signal 44 in the particle concentration range portion 150. The second table contains corresponding particle concentrations for each voltage increment of the far detector signal 46 in the particle concentration range portion 152. The third table contains the corresponding particle concentrations for each voltage increment of the near detector signal 44 in the particle concentration range portion 158. The calibration of the particle concentration monitor for measuring the concentration of the calibrated particles is complete and the monitor can now be used to accurately measure such particle concentrations.

Figure 8:
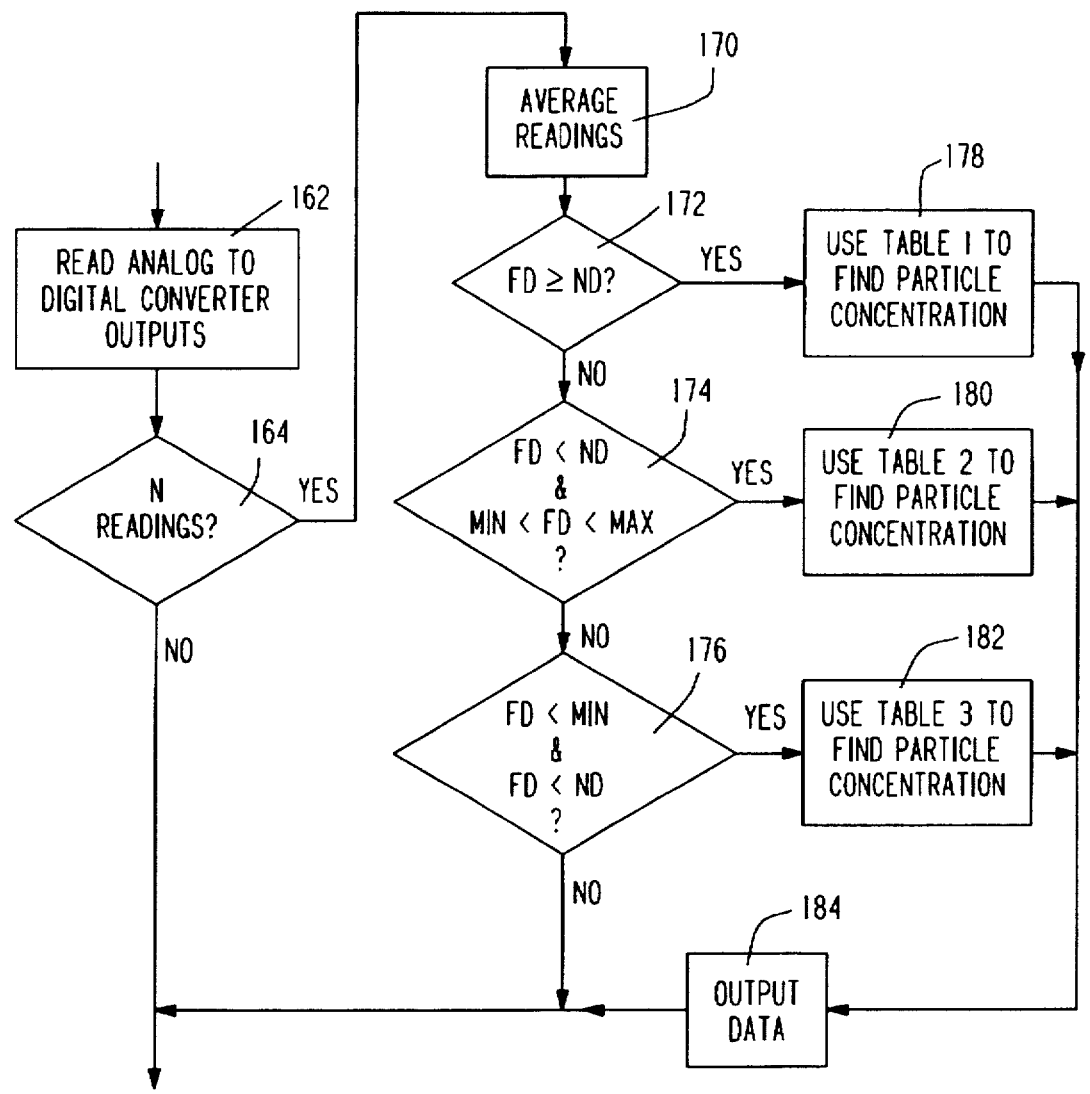
FIG. 8 is a step diagram of procedure steps employed in a computer of the circuitry of FIG. 5 to produce output data of detected particle concentration.

The procedure shown in FIG. 8 is called periodically by the computer 50 to make continuously repeated measurements of the particle concentrations. In step 162, the computer 50 reads the near light detector signal 44 and the far light detector signal 46 and saves the readings in appropriate buffers. It is then determined in step 164 if N readings have been stored in the respective buffers. If not, the program exits the procedure of FIG. 8. It is noted that steps of FIG. 8 are operated in manner, such as by timed interrupt, delay, etc., to correspond to the operating frequency waveform, such as in the range from 200 to 20,000 Hz.

Once a plurality of N readings of the near and far light detector signals have been read and stored in their corresponding buffers, the program branches at step 164 to step 170 wherein the readings in each of the near and far light detector signal buffers are averaged to compute an averaged near light detector signal ND and an averaged far light detector signal FD. This averaging in step 170 replaces the need to filter the near and for detector signals to eliminate undesired noise such as components of the operating frequency. Then in steps 172, 174 and 176 it is determined which portion 150, 152 or 158 of the particle concentration range corresponds to the near detector signal ND and the far detector signal FD. If FD is greater or equal to ND, the program branches at step 172 to step 178 where the near light detector signal ND is used to find the corresponding particle concentration in the first table (Table 1, FIG. 7) stored in the computer non-volatile memory. In step 174 when FD is less than ND and FD is also less than the minimum point 154, FIG. 6, and greater than the maximum point 156, the program proceeds to step 180 where the second table (Table 2) is used to find the particle concentration corresponding to the far detector signal FD. Step 182 and the third table (Table 3) are used to find the particle concentration corresponding to ND when step 176 finds that FD is less than both the minimum point 154 and ND. Following any of steps 178, 180 and 182 the program in step 184 outputs data, including the found particle concentration and any other measurements such as water temperature, pressure or conductivity, for transmission over the RS-232 output or temporary storage for subsequent use.

FIG. 9 is a comparison of readings made by the particle concentration monitor with actual particle concentrations. As can be seen by the graph of FIG. 9, the readings by the monitor accurately reflect the actual particle concentrations and have only minor deviations at high particle concentrations.

Figure 10:
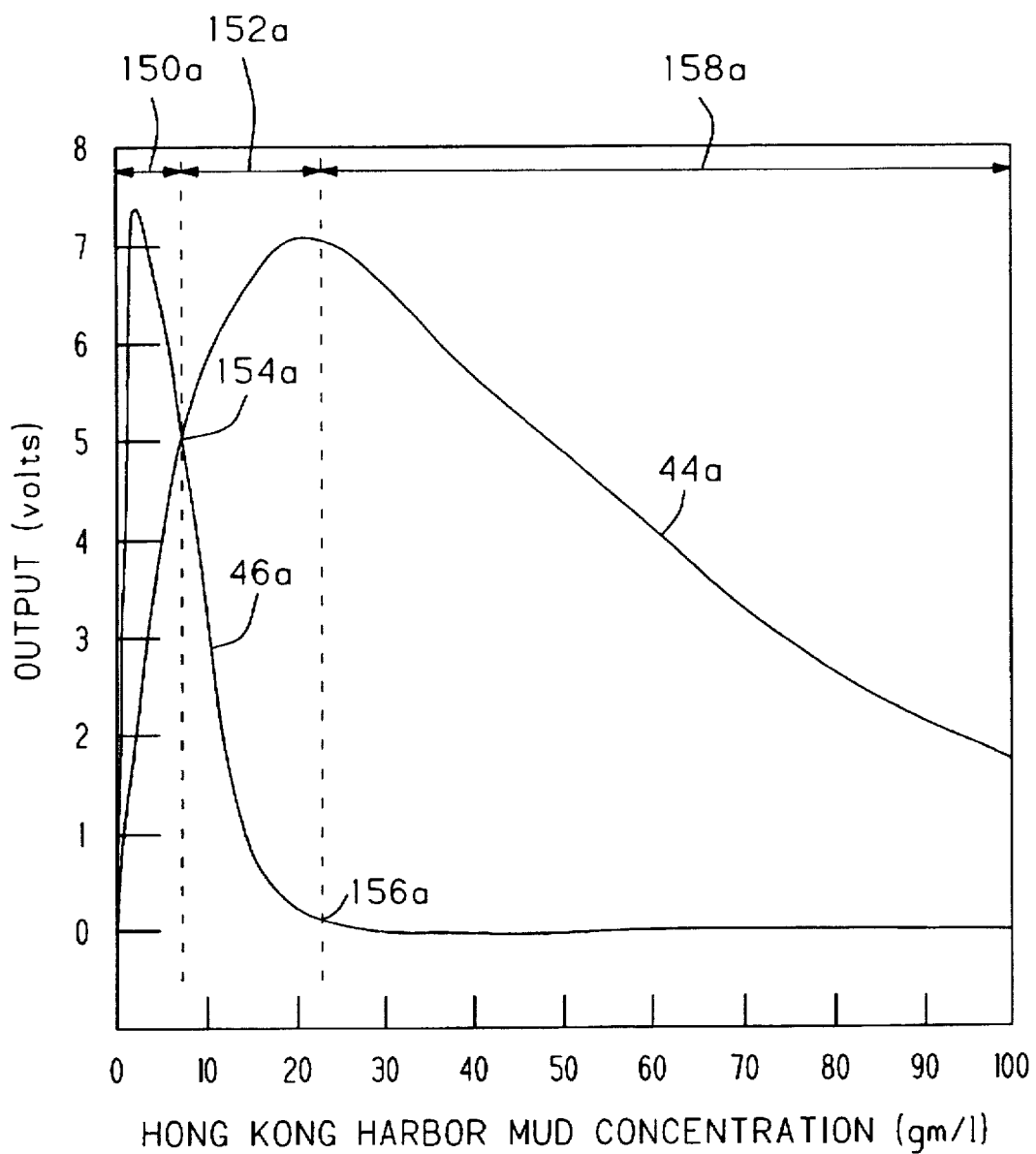
FIG. 10 is a graph similar to FIG. 6 but illustrating a different calibration and employment of back scatter radiation.

FIG. 10 is a graph showing curves of near and far light detector signals 44a and 46a over a range of particle concentrations based upon laboratory experiments detecting back scatter radiation. A monitor using back scatter radiation for detecting particle concentration in a fluid employs an arrangement, such as in FIG. 11, of a light source 30a, a near light sensitive element 32a and a far light sensitive element 34a wherein the light beam 87a from the light source is directed perpendicular to the plane of the elements 32a and 34a so that the elements 32a and 34a sense only back scatter radiation. The range of particle concentrations of FIG. 10 can be divided into portions 150a, 152a and 158a similar to that of FIG. 6 and used to generate corresponding tables for use by a computer to provide an extended range of monitored particle concentrations. As can be seen in FIG. 6, a range of particle concentrations from 0 to about 80 grams per liter can be monitored by the monitor of FIGS. 1–8. FIG. 10 illustrates that the present invention can be used for an even greater range extending above 100 grams of sediment particles per liter.

Figure 11:
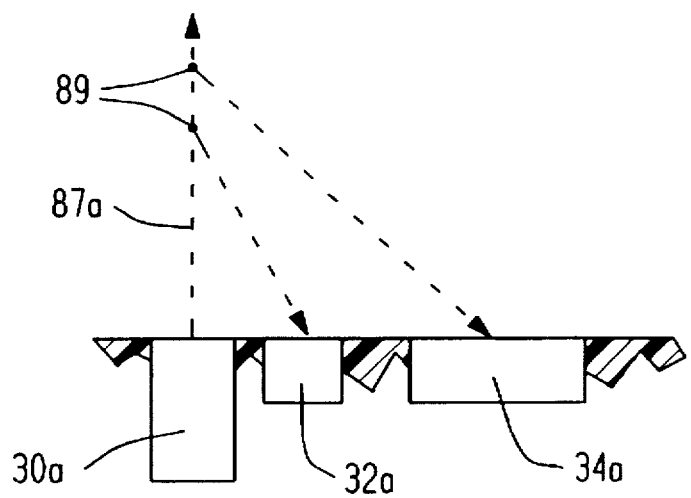
FIG. 11 is view similar to FIG. 3 but illustrating orientation of the light source to produce back scatter sensing by the near and far light sensitive elements.
Figure 12:
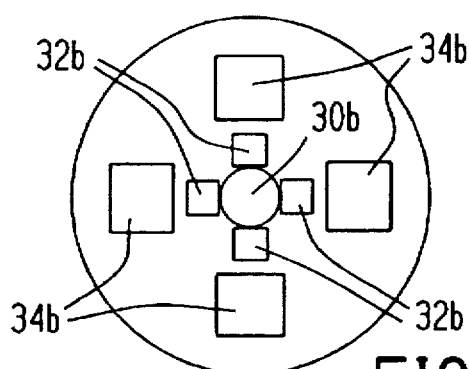
FIG. 12 is a plan view of still another arrangement of a light source with near and far light sensitive elements in accordance with the invention.

While FIGS. 3 and 11 present arrangements employing a single near light sensing element and a single far light sensing element responding to scattered light, multiple sensing elements can be combined and used for each of the near and far light sensing elements. For example as shown in FIG. 12, multiple near light sensing elements 32b and multiple far light sensing elements 34b are arranged around the light source 30b. Such employment of multiple sensing elements for either or both of the near and far light sensing elements can provide additional sensitivity and extended range.

Figures 13, 14:
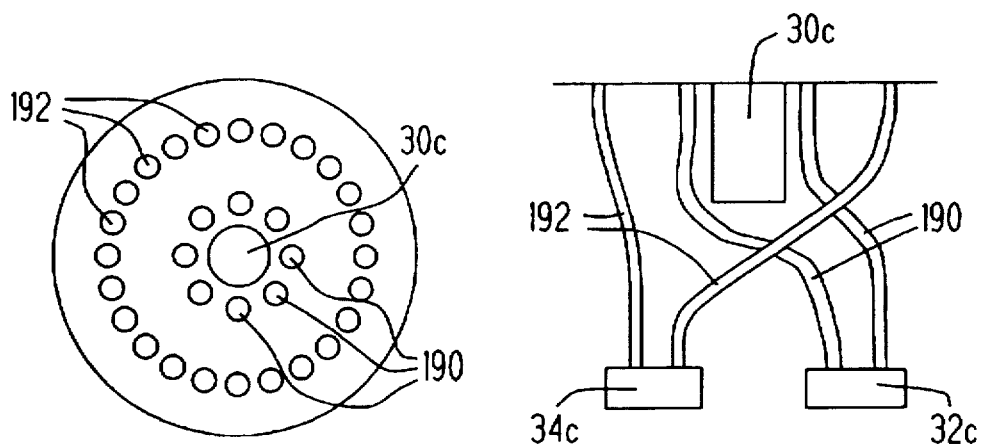
FIG. 13 is a view similar to FIG. 12 bat of a further arrangement of a light source with near and far scattered light gathering elements.
FIG. 14 is a diagrammatic section view of the arrangement of FIG. 13.

Also arrangements of light sources and far and near light sensing elements can employ various optic devices such as lenses, mirrors, prisms, optic fibers, etc., in one or more of the light paths from the light source or to the light sensing elements. FIGS. 13 and 14 illustrate one possible arrangement of optic fibers employed in the light paths to the near and far light sensing elements. A circular array of optic fibers 190 closely spaced to the light source 30c receives scattered light scattered by particles and transmits the light to the near light sensing element 32c. A circular array of optic fibers 192 spaced at a selected distance outside the array 190 receives scattered light and transmits the received light to the far light sensing element 34c.

Since many changes in detail, modifications and variations may be made to the above described embodiments of a particle concentration monitor, it is intended that the above description and the accompanying drawings be interpreted as only illustrative and not in a limiting sense.

What is claimed is:

1. A suspended particle concentration monitor comprising:
   a light source for directing radiation into clear fluid containing a volume of suspended particles;
   a near detector circuit including a near light sensitive element for generating a near detector signal proportional to radiation scattered by the suspended particles onto the near light sensitive element;
   a far detector circuit including a far light sensitive element for generating a far detector signal proportional to radiation scattered by the suspended particles onto the far light sensitive element;
   said near detector circuit and said far detector circuit being such that for a first concentration of particles the far detector signal is greater than the near detector signal and for a second concentration of particles the near detector signal is greater than the far detector signal; and
   means for analyzing said far and near detector signals to determine particle concentration in a range of concentrations including both said first concentration and said second concentration.

2. A suspended particle concentration monitor as claimed in claim 1 wherein said first concentration of particles is less than said second concentration of particles.

3. A suspended particle concentration monitor as claimed in claim 1 wherein said analyzing means bases the particle concentration on said near detector signal in a first concentration range portion including said first concentration in said range of concentrations and bases the particle concentration on said far detector signal in a second concentration range portion including said second concentration in said range of concentrations.

4. A suspended particle concentration monitor as claimed in claim 3 wherein said first concentration range portion is less than said second concentration range portion.

5. A suspended particle concentration monitor as claimed in claim 3 wherein said analyzing means includes a computer with a first table of values of the particle concentrations corresponding to values of tie near detector signal in said first concentration range portion and a second table of values of the particle concentrations corresponding to values of the far detector signal in said second concentration range portion.

6. A suspended particle concentration monitor as claimed in claim 5 wherein said first concentration range portion is less than said second concentration range portion.

7. A suspended particle concentration monitor as claimed in claim 3 wherein said analyzing means bases the particle concentration on said near detector signal in a third concentration range portion of said range of concentrations, said near detector signal being greater than said far detector signal in said third concentration range portion.

8. A suspended particle concentration monitor as claimed in claim 7 wherein said first concentration range portion is less than said second concentration range portion which in turn is less than said third concentration range portion.

9. A suspended particle concentration monitor as claimed in claim 7 wherein said analyzing means includes a computer with a first table of values of the particle concentrations corresponding to values of the near detector signal in said first concentration range portion, a second table of values of the particle concentrations corresponding to values of the far detector signal in said second concentration range portion, and a third table of values of the particle concentrations corresponding to values of the near detector signal in said third concentration range portion.

10. A suspended particle concentration monitor as claimed in claim 9 wherein said first concentration range portion is less than said second concentration range portion which in turn is less than said third concentration range portion.

11. A suspended particle concentration monitor as claimed in claim 10 wherein said first concentration range portion corresponds to near detector signal values which are less than or equal to far detector signal values; said second concentration range portion corresponds to far detector signal values less than said near detector signal values but greater than a predetermined minimum far detector signal value; and said third concentration range portion corresponds to near detector signal values greater than far detector signal values and less than said predetermined minimum far detector signal value.

12. A suspended particle concentration monitor as claimed in claim 1 wherein said far light sensitive element has a light collecting area which is substantially larger than a light collecting area of said near light sensitive element.

13. A suspended particle concentration monitor as claimed in claim 12 wherein said far detector circuit has a signal gain which is greater than a signal gain of said near detector circuit.

14. A suspended particle concentration monitor as claimed in claim 1 wherein said far detector circuit has a signal gain which is greater than a signal gain of said near detector circuit.

15. A suspended particle concentration monitor as claimed in claim 1 wherein said far light sensitive element is spaced from said light source by a distance which is greater than a distance by which said near light sensitive element is spaced from said light source; and said far detector signal and said near detector signal have peak magnitudes at different corresponding particle concentrations and which differ by less than 30%.

16. A suspended particle concentration monitor as claimed in claim 15 wherein the peak magnitudes of said far detector signal and said near detector signal differ by less than 10%.

17. A suspended particle concentration monitor as claimed in claim 15 wherein said far light sensitive element has a light collecting area which is substantially larger than a light collecting area of said near light sensitive element.

18. A suspended particle concentration monitor as claimed in claim 17 wherein said far detector circuit has a signal gain which is greater than a signal gain of said near detector circuit.

19. A suspended particle concentration monitor as claimed in claim 15 wherein said far detector circuit has a signal gain which is greater than a signal gain of said near detector circuit.

20. A suspended particle concentration monitor as claimed in claim 1 wherein said light source, said near light sensitive element and said far light sensitive element are mounted in a head having a flat surface with respective windows arranged in a line and through which said light source, said near light sensitive element and said far light sensitive element are exposed to the volume of suspended particles;

said light source directs a beam of radiation from its corresponding window at a angle of about 45° over the window of said near light sensitive element and then over the window of said far light sensitive element;

said window of said near light sensitive element being spaced by a distance of from 2 to 10 mm from said window of said light source;

said window of said far light sensitive element being spaced by a distance of from 4 to 40 mm from said window of said light source;

said far light sensitive element having a light collecting area which is about 2.8 times a light collecting area of the near light sensitive element;

said far detector circuit having a signal gain which is greater than a signal gain of said near detector circuit such that said far detector signal and said near detector signal have peak magnitudes at different corresponding particle concentrations and which differ by less than 10%;

said analyzing means includes a computer with a first table of values of particle concentrations corresponding to values of the near detector signal in a first concentration range portion of said range of concentrations, a second table of values of particle concentrations corresponding to values of the far detector signal in a second concentration range portion of said range of concentrations, and a third table of values of particle concentrations corresponding to values of the near detector signal in a third concentration range portion of said range of concentrations;

said peak of said far detector signal occurring for a concentration in said first concentration range portion;

said peak of said near detector signal occurring for a concentration in said second concentration range portion;

said second concentration range portion including concentrations larger than concentrations of said first concentration range portion;

said third concentration range portion including concentrations larger than concentrations of said second concentration range portion;

said first concentration range portion corresponding to near detector signal values which are less than or equal to far detector signal values;

said second concentration range portion corresponding to far detector signal values less than said near detector signal values but greater than a predetermined minimum far detector signal value;

said third concentration range portion corresponding to near detector signal values greater than far detector signal values less than said predetermined minimum far detector signal value; and said computer having means for responding to said near and far detector signals, means for determining the concentration range of said first, second and third concentration ranges corresponding to said near and far detector signals, and for outputting a detected concentration of particles from the corresponding first, second or third tables of values of particle concentrations.

* * * * *